(12) United States Patent
Umber et al.

(10) Patent No.: US 7,568,554 B2
(45) Date of Patent: Aug. 4, 2009

(54) OIL CARTRIDGE FOR A LUBRICATOR FOR A PNEUMATICALLY DRIVEN SURGICAL HANDPIECE

(75) Inventors: Ray E. Umber, Arlington, TX (US); Steven C. Grubbs, Forney, TX (US)

(73) Assignee: Stryker Corporation, Kalamazoo, MI (US)

( * ) Notice: Subject to any disclaimer, the term of this patent is extended or adjusted under 35 U.S.C. 154(b) by 663 days.

(21) Appl. No.: 11/079,830

(22) Filed: Mar. 14, 2005

(65) Prior Publication Data

US 2005/0215984 A1 Sep. 29, 2005

Related U.S. Application Data

(60) Provisional application No. 60/556,686, filed on Mar. 29, 2004.

(51) Int. Cl.
*F16N 7/30* (2006.01)
*A61C 1/00* (2006.01)

(52) U.S. Cl. ............... 184/55.2; 184/6.14; 184/7.4; 184/55.1; 433/104

(58) Field of Classification Search ............ 184/6.14, 184/50.1, 55.1, 55.2, 58, 59; 222/189.09, 222/334; 173/DIG. 3; 261/99
See application file for complete search history.

(56) References Cited

U.S. PATENT DOCUMENTS

| 1,834,092 | A | | 12/1931 | Decrow |
| 2,845,143 | A | | 7/1958 | Wickens et al. |
| 2,865,469 | A | | 12/1958 | Lyden |
| 3,261,426 | A | * | 7/1966 | Kuhlman ............ 184/55.2 |
| 3,516,517 | A | * | 6/1970 | Kuhlman ............ 184/55.1 |
| 3,581,845 | A | * | 6/1971 | Van Nederynen ...... 184/7.4 |
| 3,652,188 | A | * | 3/1972 | Uchiyama ............ 417/511 |
| 5,161,645 | A | * | 11/1992 | Wiklund ............ 184/55.1 |
| 6,070,698 | A | | 6/2000 | Wells |
| 2003/0000774 | A1 | | 1/2003 | Highley |

FOREIGN PATENT DOCUMENTS

DE 16 00 343 A 7/1970
WO WO 03/002016 A1 1/2003

OTHER PUBLICATIONS

PCT App. No. PCT/US2005/010451, International Search Report, Jul. 2005, European Patent Office, NL.

* cited by examiner

*Primary Examiner*—Robert A Siconolfi
*Assistant Examiner*—Thomas W Irvin

(57) ABSTRACT

An oiler for supplying lubricant to a pneumatically driven surgical instrument has: a wick chamber; an oil reservoir; and a gas reservoir. The wick chamber is open to the conduit through which gas is supplied to the instrument. A wick is disposed in the wick chamber. An oil-soaked member is disposed in the wick chamber. A lubricant soaked member is disposed in the oil reservoir. The gas reservoir holds a charge of gas. When gas is supplied to the instrument, oil is educed from the wick and oil reservoir and flows with the gas stream to the instrument. Upon the shut off of the gas, the gas charge vents from the of gas reservoir. This gas delivers a charge of oil to the wick. Some of this oil is discharged from the oiler to the supply conduit. This oil lubricates the instrument when it is initially reactuated.

20 Claims, 10 Drawing Sheets

OIL CARTRIDGE FOR A LUBRICATOR FOR A PNEUMATICALLY DRIVEN SURGICAL HANDPIECE

RELATIONSHIP TO EARLIER FILED APPLICATION

This application is based on and claims priority from U.S. Provisional Patent Application No. 60/556,686, filed 29 Mar. 2004.

FIELD OF THE INVENTION

This invention is generally related to pneumatically driven surgical instruments. More particularly, this invention is directed to an oiler for providing lubricant to the motor of a pneumatically driven surgical instrument.

BACKGROUND OF THE INVENTION

In modern surgery, powered surgical tools are some of the most-important instruments medical personnel have available for performing certain surgical procedures. Many surgical tools take the form of a motorized handpiece to which a cutting accessory, like a drill bit, a bur or a saw blade, is attached. These tools selectively remove sections of hard or soft tissue or separate tissue. The ability to use powered surgical tools on a patient has lessened the physical strain of surgeons and other personnel when performing surgical procedures on a patient. Moreover, most surgical procedures can be performed more quickly and more accurately with powered surgical tools than with the manual equivalents that preceded them.

Some surgical handpieces include pneumatically driven motors. Internal to this type of handpiece is a motor that comprises a housing in which a set of vanes are located. The vanes are attached to a rotating shaft that extends out of the housing. The shaft is connected to the cutting accessory. Compressed gas is introduced into the housing. The flow of the compressed gas causes the vanes and shaft to rotate. The rotation of the shaft, in turn, causes the cutting accessory to move. Depending on the type of gear assembly used to couple the cutting accessory to the shaft, the accessory may rotate in a unidirectional pattern, oscillate around an axis, reciprocate back and forth along a longitudinal axis or oscillate back and forth along a sagital plane. The exact motion that the cutting accessory undergoes is a function, of the design of the handpiece and the gear assembly used to transfer the rotational moment of the shaft to the cutting accessory.

An advantage of a pneumatically driven surgical handpiece is that, when it is operated for an extended period of time, the temperature of the handpiece does not appreciably rise.

The efficient operation of a pneumatically driven surgical handpiece is facilitated by the inclusion of aerosol of oil in the pressurized gas supplied to the motor. The oil lubricates the interface between the vanes and the adjacent inner surface of the motor housing. The oil both reduces wear on the vanes and minimizes the noise generated as a consequence of the vanes moving against the housing.

A number of assemblies are available to supply the oil aerosol to the compressed gas stream supplied to a surgical tool. However, some of the assemblies require a significant amount of disassembly in order to refill their oil reservoirs. Still other assemblies require manual setting before surgery. A limitation associated with some assemblies is that they do not supply adequate quantities of oil to the handpiece motors when the motors are initially cycled on. Consequently, for a short period of time when the handpiece is first actuated, it runs "dry". As a result, when the handpiece is initially actuated, until the vanes are properly lubricated, the vanes are subjected to significant wear and the motor generates an appreciable amount of noise.

There have been efforts at providing oilers that operate based on the Venturi principal. This type of oiler has an opening exposed to the gas flow to the handpiece motor. The flow of the pressurized gas induces the flow of oil out of the oiler. Some of these assemblies are constructed to have wicks in their openings. The wicks regulate, dampen, the flow of oil out of the oilers. A disadvantage of these oilers is that they tend to supply excess oil during the initial period in which their complementary motors are actuated. It is further observed the wicked versions of these oilers tend to not deliver sufficient oil at the end stage of the use cycle.

During a surgical procedure, a handpiece is cycled on and off a number of times. Owing to the repetitive on and off operation, the number of times during a surgical procedure the handpiece is run dry, the wear to which the vanes can be exposed can be significant.

Also, as mentioned above, the cycling of the motor on and off with an in-line oiler often results in the delivery of excess oil during the initial stage of the use cycle. The introduction of this unneeded oil into the motor can reduce the performance of the motor. Moreover, the excess oil has a tendency to leak from the tool assembly. Clearly, this is something that should be avoided in a surgical environment. Moreover, this excess discharge can occur each time the motor is cycled on. Collectively, these excess discharges can cause the unnecessary and undesirable exhaustion of the oil supply. When this occurs, the surgical procedure may even need to be interrupted in order to refill or replace the oiler.

SUMMARY OF THE INVENTION

This invention is related to a new and useful lubricator, oiler assembly, for lubricating powered surgical tools. The oiler assembly of this invention includes a housing that has at least three chambers. At a minimum, a first chamber that functions as an oil reservoir. There is a second chamber, a wick chamber. A third chamber functions as a gas reservoir. Oil or other lubricant for lubricating the handpiece motor is stored in a saturated porous member disposed in the oil reservoir. The wick chamber is located between the oil reservoir and the conduit through which pressurized gas is flowed to the pneumatic assembly. A porous member is typically disposed in the wick chamber. A charge of pressurized gas is stored in the gas reservoir. The oiler assembly is constructed so that there is fluid communication from the gas reservoir into the oil reservoir and from the oil reservoir into the wick chamber.

Normally, the lubricant is educed out of the housing by the gas stream supplied to the handpiece motor. Specifically, the lubricant is educed out of the wetted porous member in the wick chamber. This member is wetted from the lubricant supplied from the oil reservoir.

When the handpiece motor is cycled off, the pressurized charge of gas in the gas reservoir forces a quantity of oil from the oil reservoir into the wick chamber. A fraction of this volume of oil is discharged as bolus of oil out of the housing. This oil is discharged into the gas inlet line connected to the motor. When the handpiece is turned back on, this oil is transported to the motor. This oil serves as an initial lubricant to the motor. The remaining fraction of the end head of oil held in the wick chamber after the motor cycled off is, when the motor is cycled back on, is immediately entrained into the pressure stream directed to the motor.

It is another feature of this invention to form the invention as a cartridge that is removably locked to an outer housing. The cartridge functions as the housing containing the wick chamber, the oil reservoir and the gas reservoir.

The invention is primarily directed to an oiler that can be used with surgical tools. The oiler of this invention can further be used to supply lubricant to other pneumatically actuated motors and drive units.

BRIEF DESCRIPTION OF THE DRAWINGS

The invention is pointed out with particularity in the claims. The above and further features of the invention may be better understood by reference to the following description taken in conjunction with the accompanying drawings in which:

SUMMARY OF THE INVENTION

Figure 1:
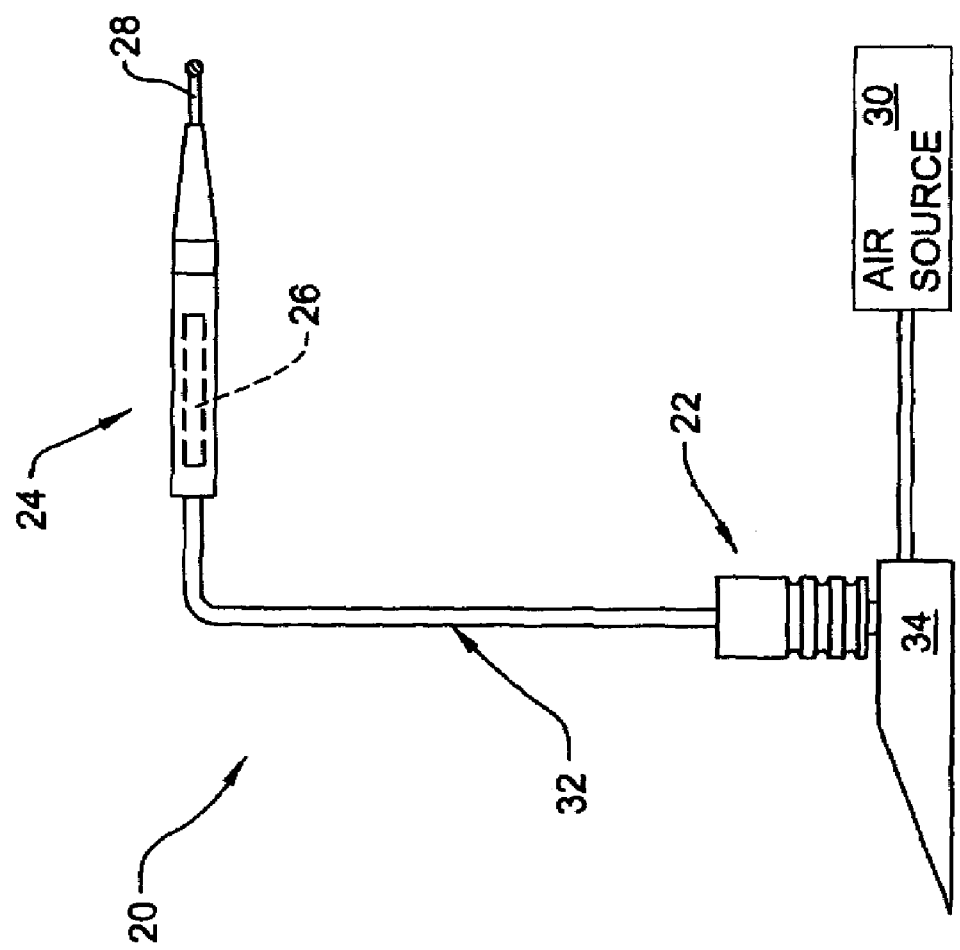
FIG. 1 is a block diagram of the components of pneumatically driven surgical tool system including the oiler assembly of this invention.

FIG. 1 illustrates a pneumatically driven surgical tool assembly 20 that includes an oiler assembly 22 constructed in accordance with this invention. Tool assembly 20 includes a surgical handpiece 24. Internal to the handpiece 24 is a pneumatically actuated motor 26 (represented by a phantom rectangle) the structure of which is not relevant to this invention. A cutting accessory 28 is attached to the distal end of the handpiece 24. ("Distal", in the specification, it shall be understood, shall mean towards the surgical site to which the cutting accessory 28 is applied. "Proximal", in the specification, it shall be understood, shall mean away from the surgical site.) A gear assembly, (not illustrated), converts the rotary motion of the shaft integral with the motor 26 into a motion that displaces the cutting accessory 28 in an appropriate manner.

Compressed gas from a source 30 is supplied to the handpiece motor 26 through an inlet line 32. In FIG. 1, source 30 is depicted as an "air" source. It should be understood this is exemplary, not limiting. The source may be a source of any pressurized gas suitable for actuating the motor 26. Nitrogen and compressed air are often used to energize a pneumatic motor. Other gases may alternatively be employed.

The flow of gas is regulated by the surgeon to actuate the motor 26 with a footswitch assembly 34. The footswitch assembly 34, series-connected between gas source 30 and inlet line 32, includes a valve assembly (not illustrated) that controls the flow of gas to the handpiece motor 26.

Oiler assembly 22 is connected at one end to the outlet bore of the footswitch assembly 34 (bore not illustrated) and at the opposite end to the proximal end of inlet line 32. As seen by reference to FIGS. 2-4, the oiler assembly includes a housing 38. Internal to the housing 38 is a removable cartridge 40. Cartridge 40 contains oil or other lubricant for lubricating handpiece motor 26. Compressed gas flows through the oiler housing 38 and cartridge 40. The gas flow educes the oil out of the cartridge 40 so that the oil is delivered to the motor 26 as part of the compressed gas stream.

Oiler housing 38 includes a head piece 42 that is the most proximal component of the oiler assembly 22. Head piece 42 is shaped to have a threaded stem 44. The threading facilitates the mating of the oiler assembly 22 to a complementary threaded bore that forms the outlet bore of the footswitch assembly 34. Extending distally from stem 44, head piece 42 has a relatively wide diameter center section 46. A threaded tail 48 extends distally from head piece center section 46. Tail 48 has an outer diameter similar to that of stem 44. Head piece 42 further has a bore 50 that extends axially therethrough. There is also a counterbore 52 that extends proximally from the open end of head piece tail 48 and partially through center section 46.

An inner shell 54, also part of oiler housing 38, extends distally from the head piece tail 48. The inner shell 54, which is generally tubular shaped, has a proximal end neck 56. The inner surface of the neck 56 is formed with threading, not identified, that engages the threading along the outer surface of head piece tail 48. The neck 56 is further formed to have an annular lip 58 that extends inwardly from the inner surface of the neck towards the longitudinal axis of the inner shell 54. The inner shell 54 also has a main body 60 that is integral with and located distally from the neck 56. Main body 60 has inner and outer diameters that are both greater than the respective inner and outer diameters of the neck 56.

Figure 3:
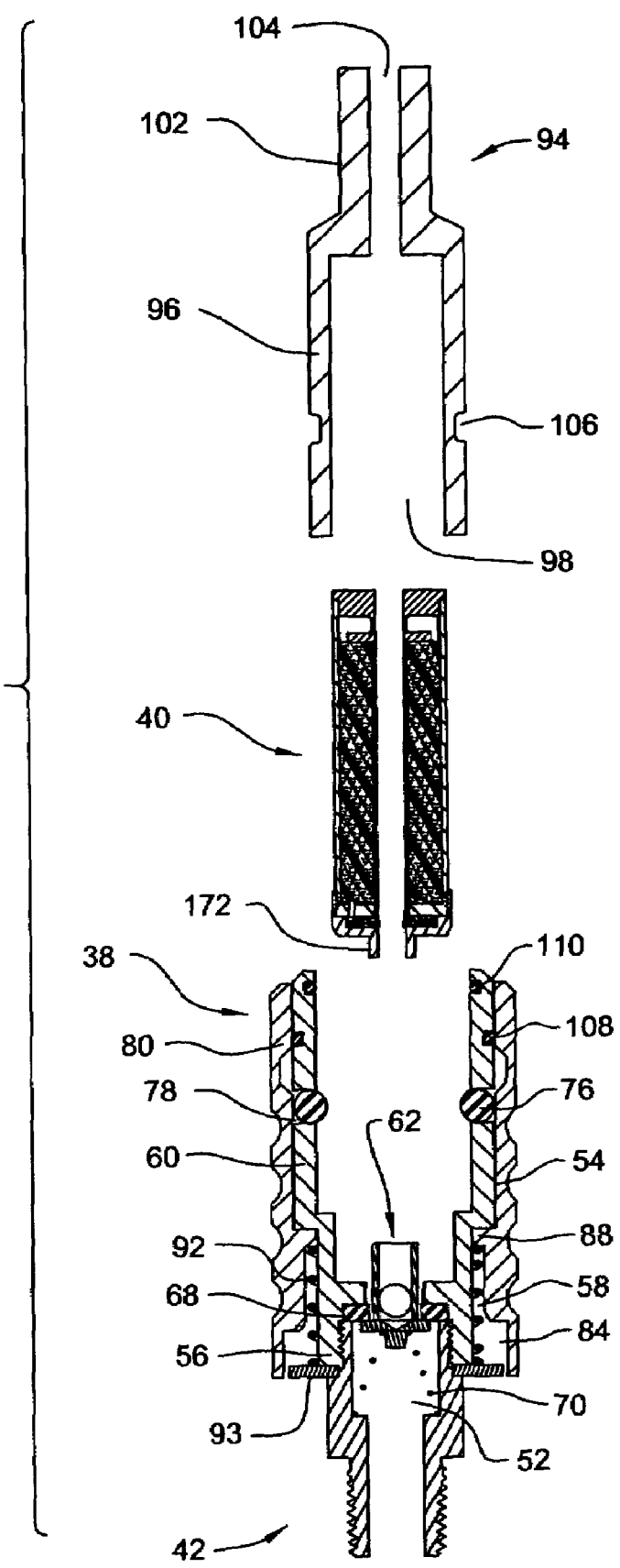
FIG. 3 is longitudinal sectional view of a disassembled oiler assembly of this invention.
Figure 4:
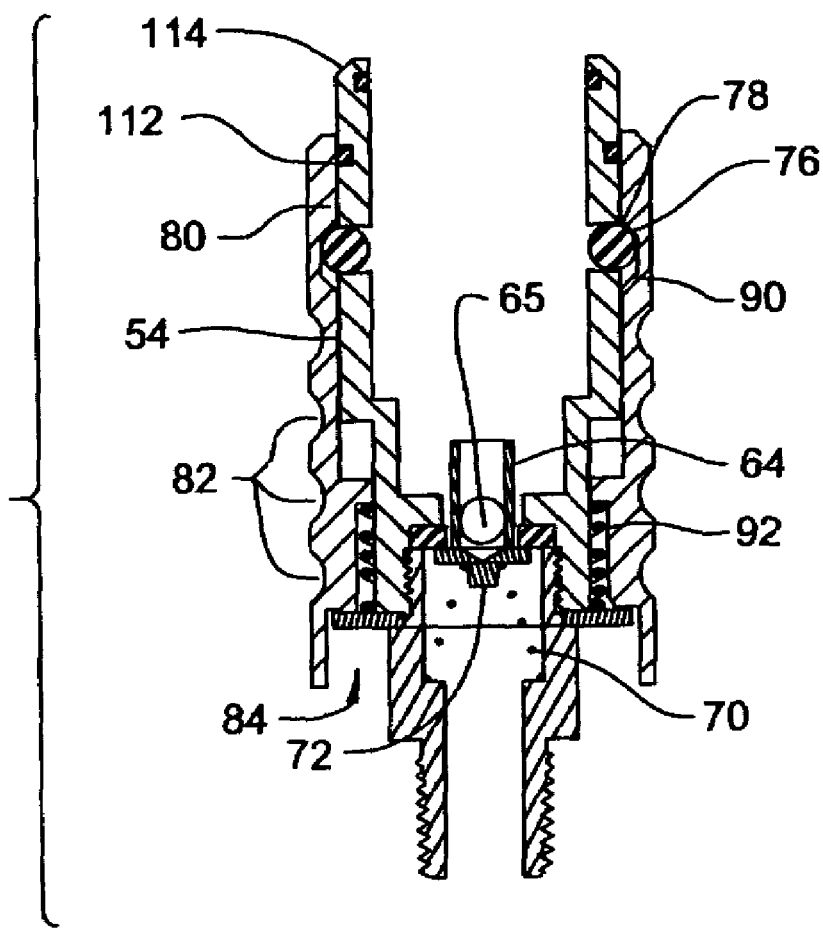
FIG. 4 is a longitudinal sectional view illustrating the proximal end of the oiler housing when the housing is in the open state.

A valve assembly 62, now described by reference to FIGS. 3 and 4, is located between the head piece 42 and the inner shell 54 to regulate gas flow through the oiler assembly 22. The valve assembly 62 includes a valve member 64 with a tube-shaped main body that extends through the space defined by the annular shaped face of inner shell lip 58. Valve member 64 has a cap 66 that has a wider diameter than the main body and that is located over the proximal end of the main body. The main body of valve member 64 defines openings 65 (one shown) that extend into the center space within the main body.

The valve member cap 66 is seated in the distal end of head piece counterbore 52. The distally-directed outer surface of the cap 66 seats against a seal 68 that is disposed over the proximally directed face of the inner shell lip 58. When the oiler housing 38 is assembled, seal 68 is disposed over the lip 58 prior of the mating of the head piece 42. Then, when the head piece tail 48 is secure secured in the inner shell neck 56, the seal 68 is compression fitted between the distal end face of the tail and the shell lip 58.

A conical-shaped spring 70 normally holds the valve member 64 in the closed position. Spring 70 is seated in counterbore 52. Specifically, the wide diameter end of the spring 70 is seated against the annular surface in the head piece center section 46 that defines the base of the counterbore 52. The narrow diameter end of spring 70 presses against valve member cap 66. To prevent the distal end of the spring from shifting position, valve member cap 66 has a small outwardly extending boss 72. The distal end of the spring 70 seats over the boss 72.

Two opposed ball bearings 76 are seated in the housing inner shell main body 60. Specifically, the main body 60 is formed with two diametrically opposed inwardly tapered bores 78. Bores 78 have inner diameters that are equal to approximately one-quarter to one-third the inner diameter of the bearings 76. Thus, ball bearings 76 can protrude into the inner shell main body 60 but cannot fall into the inner shell 54. While the invention is shown as having two ball bearings 76, in some versions, more than two ball bearings may be provided.

The oiler housing 38 also includes a sleeve-shaped outer shell 80 that is slidably disposed over the inner shell 54. Outer shell 80 has a generally constant outer diameter. There are, however, parallel, annular concave grooves 82 formed around the proximal end of the outer shell 80. Grooves 82 define a finger grasping surface to facilitate grasping the sliding of the shell 80.

Outer shell 80 is further formed to have a first wide diameter mouth 84 that defines the proximal end opening into the shell. Immediately distal to mouth 84, the shell 80 has a first lip 86 that extends inwardly towards the longitudinal axis of the oiler housing 38. Integrally formed with and at the distal end of the first lip 86, the outer shell 80 is shaped to have a second lip 88. The second lip 88 is smaller in longitudinal length than the first lip 86 and projects further toward the center axis of the housing 38 than the first lip 86. Extending distally from the second lip 88, the outer shell 80 has a generally constant inner diameter that facilitates a close sliding fit between the outer shell and the adjacent inner shell main body 60. A groove 90 formed in the inner surface of the outer shell 80 extends inwardly relative to the inner surface and circumferentially around the shell 80.

When the oiler housing 38 is assembled, the inner shell neck 56 seats in the outer shell mouth 84 and the annular spaces defined by the shell first and second lips 86 and 88, respectively. The distal facing end surface of the outer shell second lip 88 seats against the adjacent outer stepped surface between the neck 56 and main body 60 of the inner shell 54.

A coil spring 92 normally holds the outer shell 80 in the above-described position relative to the inner shell 54. The distal end of spring 92 seats against a washer 93 or other ring shaped member that is disposed over the head piece 42. More particularly, the inner perimeter section of the washer 93 is sandwiched between the stepped surface between the head piece center and tail sections 46 and 48, respectively, and the proximal end of the inner shell neck 56. Spring 92 extends distally around the inner shell neck 56 in an annular gap between neck 56 and the adjacent outer shell first lip 86. The distal end of the spring 92 bears against the proximally-directed exposed face of the outer shell second lip 88.

Oiler housing 38 includes a cap 94 that is removably fitted over the cartridge 40. Cap 94 has a generally cylindrical base 96. The cap base 96 has an outer diameter that allows for a close sliding fit into the void space defined by the inner surface of the inner shell main body 60. Cap base 96 has a center opening 98 designed to accommodate, in close sliding fit, cartridge 40.

Extending distally from the closed end of base 96, the cap 94 has a head 102 integral with the base. Head 102 has an outer diameter less than that of the base 96. A bore 104 extends longitudinally axially through head 102 from the base of opening 98 to the distally directed end of the head. While not illustrated, it should be appreciated that the head may be provided with coupling features designed to engage complementary coupling member on the proximal end of the inlet line 32 in order to allow the two components to be releasably connected together.

Ball bearings 76 releasably hold the cap 94 to the other components of the oiler housing 38. Specifically, the cap base 96 is formed with a groove 106 that extends circumferentially around the outer surface of the base. The cap 94 is fitted to the rest of the housing 38 by first pressing downwardly on the outer shell 80. This places outer shell groove 90 in registration with the ball bearings 76. Cap 94 is then slid into the void space within the inner shell main body 60. This component seating is possible because, upon the abutment of the cap 94 against the ball bearings 76, the bearings move into the groove 90 as seen in FIG. 4. Once the cap 94 is so seated, force on the outer shell 80 is released. Spring 92 then urges the outer shell 80 back to the static position. The movement of the outer shell 80 causes the bearings 76 to be pressed inwardly by the outer surface of the shell 80. The bearings 76 seat in cap groove 106 to hold the cap 94 in position.

Housing inner shell 54 is provided with two O-rings 108 and 110. O-ring 108 is seated in a groove 112 that extends circumferentially around the outside of the inner shell main body 60 above bores 78. O-ring 108 forms a seal between the inner shell main body 60 and the outer shell 80. O-ring 110 is seated in a groove 114 formed in the inside surface of the shell main body 60 that is located above groove 112. O-ring 110 thus functions as a seal between the distal end of the inner shell 54 and cartridge 40.

The structure of the cartridge 40 is now described by reference to FIGS. 5-9. Specifically, the cartridge includes a generally cylindrical housing 118. The housing defines a first chamber, oil reservoir 120, in which oil for lubricating the handpiece motor 26 is stored. With allowances for through holes, the purpose of which is discussed below, the proximal end of the housing 118, which defines the base of oil reservoir 120, is closed. A cap 122 is secured over the proximal end of the housing 118.

Figure 6:
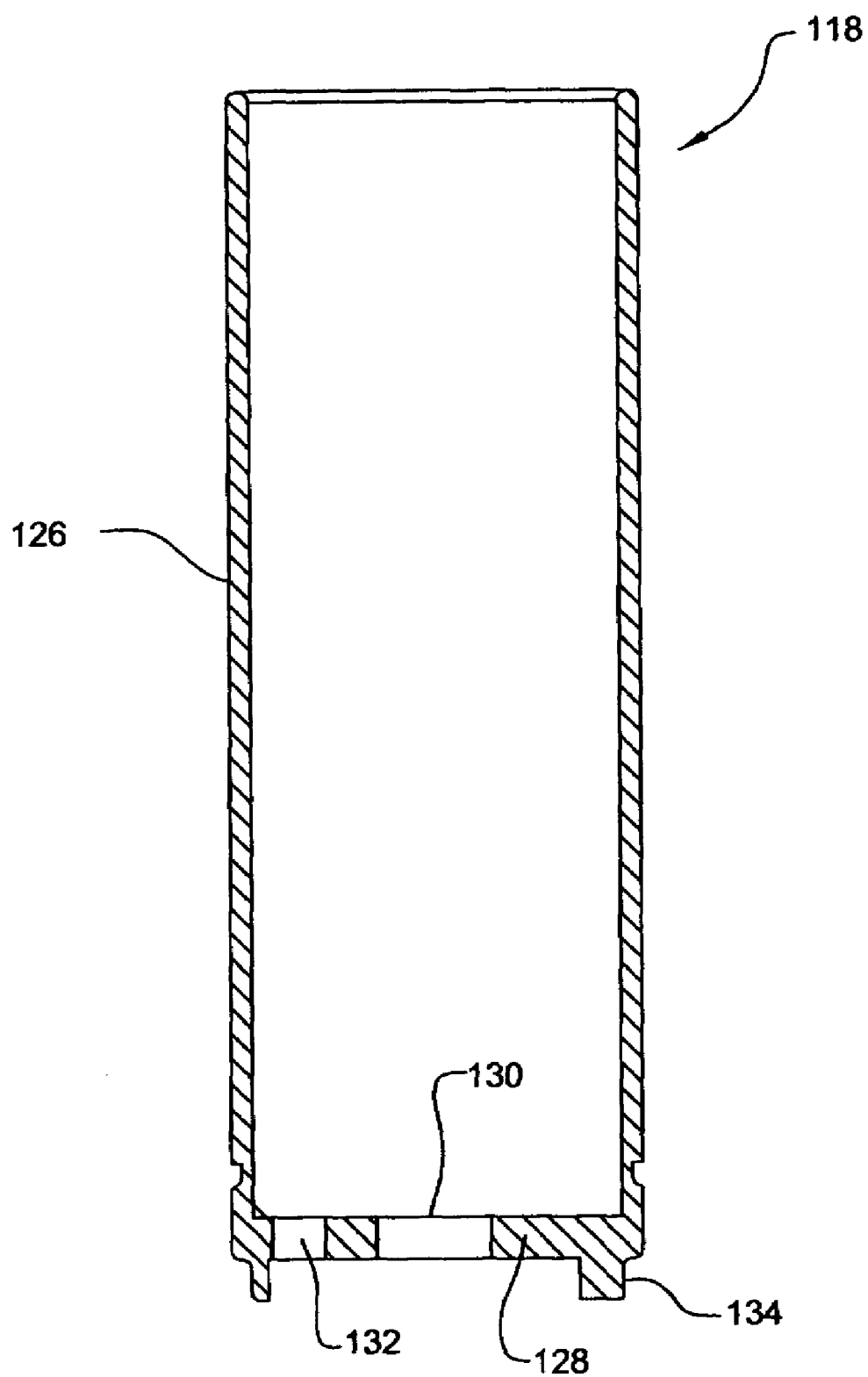
FIG. 6 is a longitudinal sectional view of the housing of the oiler cartridge.

As seen best by FIG. 6, the cartridge housing 118 has a body 126 in the form of a sleeve that is open towards the distal end of the cartridge 40. A circular end plate 128 is formed integrally with and closes the proximal end of the housing body 126. The end plate 128 is formed with two through holes 130 and 132 that open into the void space defined by body 126. Hole 130 is coaxial with the longitudinal axis of the cartridge housing 118. Hole 132 is located to one side of hole 130. Hole 130 is larger in diameter than hole 132.

Cartridge housing 118 is further formed to have a circular lip 134 that is integral with and extends proximally away from end plate 128. Lip 134 thus extends in a direction parallel to the longitudinal axis of the cartridge housing 118. Lip 134 is positioned so as to be located slightly inward of the inner surface of the wall that defines the housing body 126.

When cartridge 40 is assembled, cap 122 seats over and around housing lip 134. Thus, cap 122, housing end plate 128 and lip 134 collectively define a circular wick chamber 135.

Figure 5:
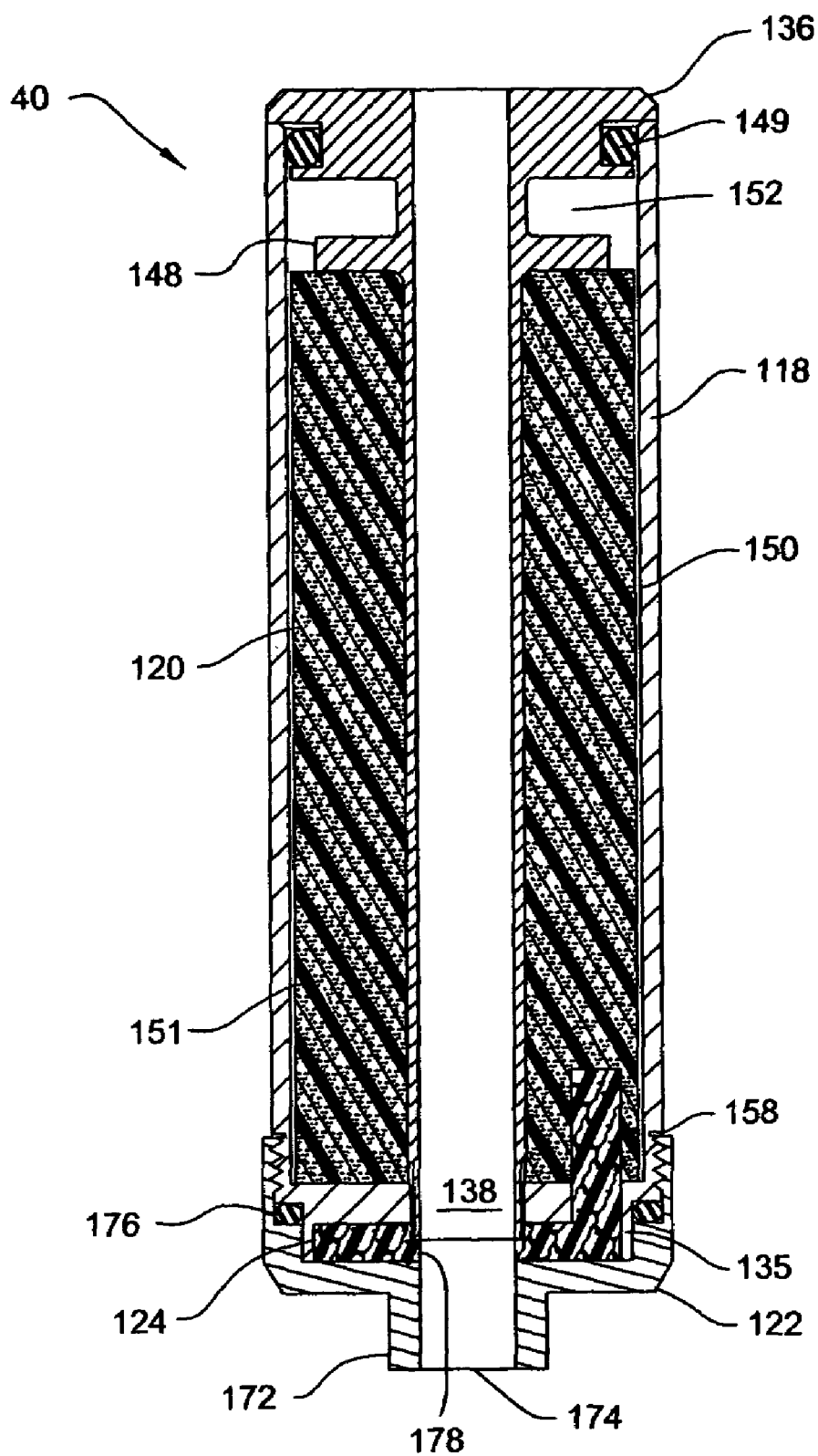
FIG. 5 is a longitudinal sectional view of the cartridge.
Figure 7:
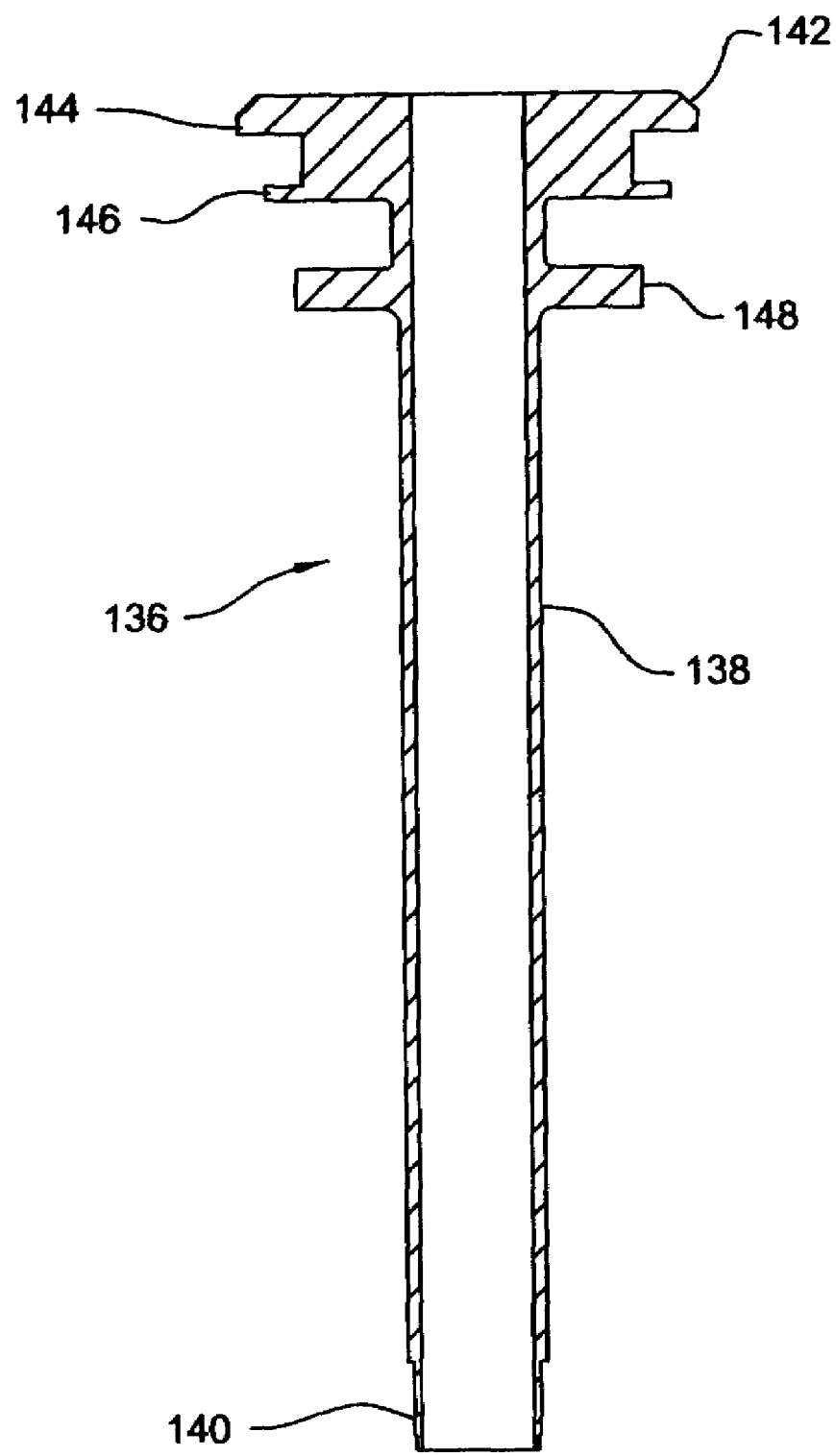
FIG. 7 is a longitudinal sectional view of the oiler cartridge core.

A core 136, seen best in FIGS. 5 and 7, extends over the open end distal end of the housing body 126 and through the housing body. Core 136 has tube shaped stem 138 that is open at both the proximal and distal ends More particularly, the core 136 is formed so that when the cartridge 40 is assembled, stem 138 extends through the housing body 126, through end plate 128 and projects a short distance beyond the outer face of the end plate so as to terminate short of cap 122. In the depicted version of the invention, the proximal end 140 of the stem 138 has a reduced outer diameter. More specifically, the diameter of stem proximal end 140 is such so that the stem seats tightly in end plate hole 130.

A generally circular head 142 that extends around the distal end of stem 138 forms the distal end of the core 136. The head 142, which is formed integrally with the stem 138, has a circumferentially extending upper lip 144 that projects laterally away from the longitudinal axis of the core 136. Upper lip 144 is formed to have an outer diameter equal to that of the outer diameter of the housing body 126. Core head 142 also has a circumferentially extending lower lip 146 spaced proximally away from the upper lip 144. Lower lip 146 has an outer diameter that facilitates a close slip fit of the lip into the void space within the distal open end of the housing body 126.

Core 136 also has a disk shape shoulder 148 also integrally formed with the stem 138. Shoulder 148 is spaced proximally from the head 142 and, like the head, extends laterally away from the longitudinal axis of the core 136. Shoulder has an outer diameter that is less than the diameter of the inner surface of the housing body 126 such that the two components are spaced apart from each other.

When the cartridge 40 is assembled, the upper lip 144 of the core head 142 covers the open distal end of the housing body 126 so as to function as a cap over the housing body. An O-ring 149 is seated in the annular gap between the head upper and lower lips 144 and 146, respectively. The O-ring 149 thus forms a seal around the distal end of the cartridge 40.

The oil reservoir 120 is defined by the annular space inside the housing body 126 between the inner surface of the body 126 and the outer surface of the core stem 138. The oil reservoir 120 extends from the distally-directed surface of end plate 128 to the proximally facing surface of the core shoulder 148. A sleeve 150 formed of a porous oleophilic material is disposed in oil reservoir 120. In some versions of the invention, sleeve 150 is formed from an oleophilic, open cell foam. Suitable foams are ethyl ether or polyethylene foams. Other foams may, of course, be employed as the material from which sleeve 150 is formed.

Sleeve 150 extends outwardly from the core stem 138 towards the inner surface of the housing body 126. The sleeve 150, however, does not tightly seat against the inner surface of the housing body 126. In some versions of the invention, especially when the sleeve is formed from incompressible porous material, the sleeve may actually be dimensioned to be spaced a slight distance inwardly from the inner surface of the housing body. This distance may be up to 50% of the radius from the center of the cartridge. This separation, defines an annular channel 151 between the sleeve and the housing body 126. Channel 151 extends from the proximal end of the sleeve to the distal end. Sleeve 150 is shaped and positioned to be seated at least substantially, if not completely, over end plate hole 132. Sleeve 150 is saturated with the lubricant used to lubricate the handpiece motor 26.

Cartridge 40 also has a third chamber, gas reservoir 152. Gas reservoir 152, which has an annular cross sectional profile, is defined by the gap between the core head 142 and shoulder 148. The gas reservoir 152, like oil reservoir 120, extends between the inner surface of the housing body 126 and the core stem 138. The gas reservoir 152 is in communication with the oil reservoir 126 through the annular gap between the inner surface of the housing body 126 and the core shoulder 148. The annular channel defined by the inner wall of the housing body 126 and sleeve 150 extends to the gas reservoir 152. The function of the gas reservoir 152 is discussed below.

Figure 9:
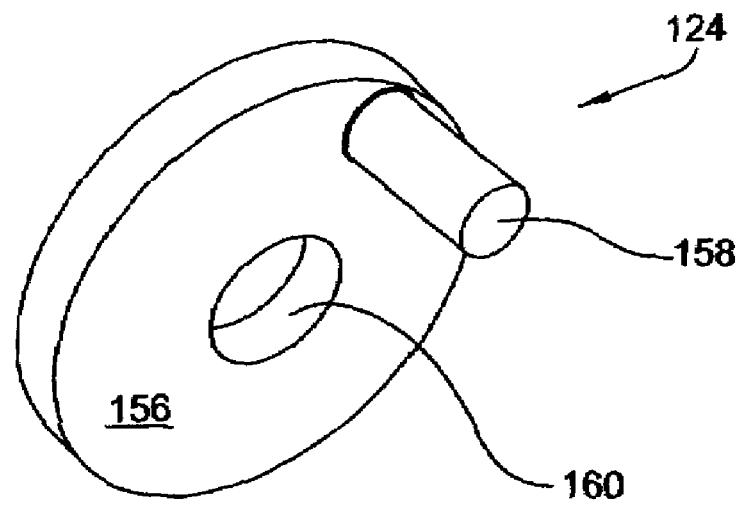
FIG. 9 is a perspective view of the wick internal to the oiler cartridge.

A wick 124 is disposed in wick chamber 135. The wick 124, described by reference to FIG. 9, is formed of a porous wicking material such as an open cell, porous plastic sold under the trademark Porex by the Porex Corporation of Fairburn, Ga., USA, or porous polyethylene plastic. Wick 124 has a disk-shaped body 156. The outer diameter of the wick body 156 is selected to facilitate the tight seating of the body in the wick chamber 135 defined by lip 134 of the cartridge housing 118. Wick 124 has a cylindrical nib 158 that extends from one face of the body 156. Wick body 156 is formed to have a center-located through hole 160. Through hole 160 is dimensioned to facilitate the snug fitting of the wick body 156 around the core stem proximal end 140.

When cartridge 40 is assembled, the wick 124 is seated over the exposed face of the housing end plate 126. Nib 158 extends through the end plate hole 132 into the oil reservoir 120. More particularly, the nib 158 is positioned to be in contact with the oil saturated sleeve 150. Nib 158 is dimensioned to extend through housing end plate 128. In preferred versions of the invention, nib 158 is shaped so that the section that extends beyond end plate 128 into oil reservoir 120 is at least 10% of the total overall length of the nib. In some versions of the invention, sleeve 150 has a closed end bore in which the nib 158 is seated.

Figure 8:
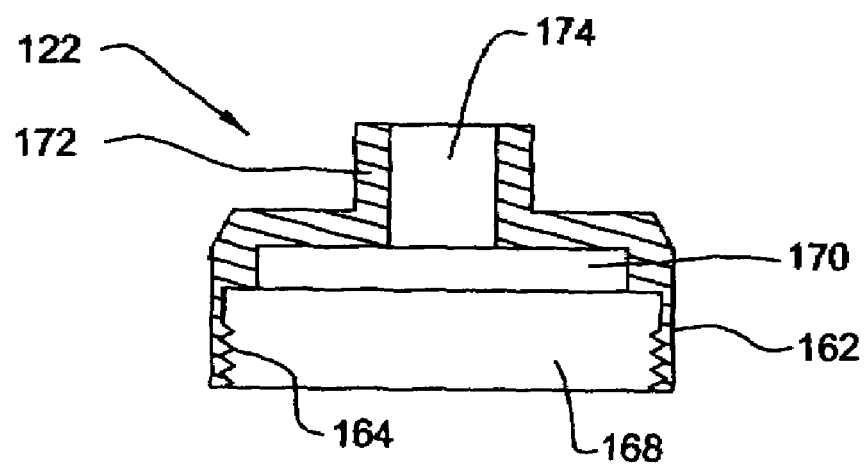
FIG. 8 is a longitudinal sectional view of oiler cartridge cap.

Cap 122, illustrated in FIGS. 5 and 8, covers the wick 124 so as to fully define wick chamber 135. The cap 122 is formed of metal or plastic. The cap 122 is shaped to have a circular, open-ended base 162. The circular inner wall of the base 162 is provided with threading 164. When the cartridge 40 is assembled, the threading 164 engages complementary threading formed around the proximal end the housing body 126 to hold the cap 122 to the cartridge housing 118 (housing threading not identified). The open space defined by the cap threading 164 is the cap mouth 168.

Extending proximally from the cap mouth 168, upwardly from the mouth in FIG. 8, the cap base 162 is formed to have a circular void space 170. The cap 122 is formed so that the space 170 has a diameter that allows the cap lip 134 to be closely slip fit into space 170. This diameter is less than the diameter of the cap mouth 168. A circular boss 172 extends proximally away from the cap base 162. Boss 172 is centered along the longitudinal axis of the cap 122. The boss is formed to have a through bore 174 that opens into the wick chamber 170. Cap 122 is further formed so that boss 172 has an outer diameter substantially equal to the outer diameter of valve member 64.

When cartridge 40 is assembled, the cap 122 is screw secured over the wick 124 and to the cartridge housing body 126. The extent to which the cap 122 fits against the wick body 156 is limited by the abutment of the cap interior surface that defines the base of the wick chamber 170 against housing lip 134. An O-ring 176 is seated around the outer perimeter of the housing lip 176. When the cap 122 is fitted to the housing, the O-ring 176 is sandwiched between the outer perimeter of the housing end plate 128 and the annular stepped surface of the cap between mouth 168 and wick chamber 170. O-ring 176 forms a seal around the proximal end of the cartridge housing 118 and cap 122.

Collectively, the cap 122, the wick 124, the housing lip 134 and the core stem 138 are dimensioned so that, when the cartridge 40 is assembled, a small circular surface 178 of the wick body 156 that defines hole 160 is exposed. This surface 178 is located adjacent the gap between the proximal end of the core stem 138 and the inner surface of the cap 122 that defines the base of void space 170, which is also the base of the wick chamber 135. Generally, the components forming cartridge 40 are shaped so that the exposed surface 178 of wick 124 has an overall length between 10 and 100% of the depth of the wick chamber 135.

Returning to FIGS. 2 and 3, it can be seen that the cartridge 40 is inserted into the oiler housing 38 by directing the cap end towards valve assembly 62. Cap boss 172 thus presses against the valve member 64. The proximal end of the cartridge, the cap 122 and the proximal end of the housing body 126 are seated in the void space defined by the inner shell neck 56 that is distal of shell lip 58. The housing cap 94 is pressed over the portion of the cartridge 40 that is located distally from the shell neck 56. Ball bearings 76 seat in groove 106 of the housing cap 94 to hold the cap to the rest of the oiler housing 38.

Figure 2:
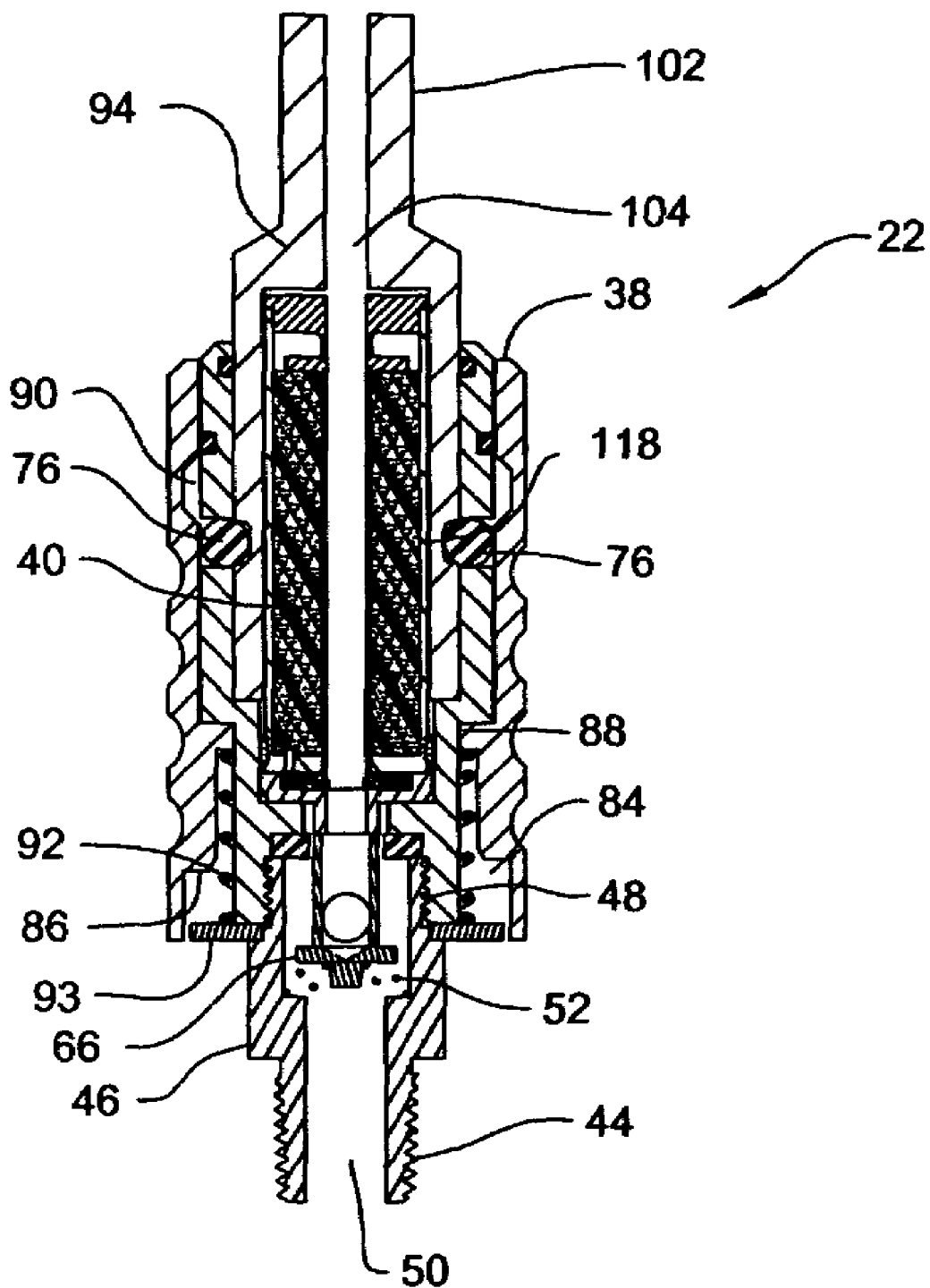
FIG. 2 is a longitudinal sectional view of the assembled oiler assembly.

As a consequence of the seating of the cartridge 40 in the housing 38, cartridge cap boss 172 overcomes the force of spring 70 to push the valve member 64 in a proximal direction. The movement of the valve member cap 66 away from seal 68 causes the valve member openings 65 to move into counterbore 52 of the headpiece 42 as seen in FIG. 2.

When a surgeon actuates the handpiece 22 of system 20, gas flows from the footswitch assembly 34, through oiler assembly 22 and inlet line 32 into the motor 26. Within the oiler assembly 22, the gas flows into head piece bore 50 and counterbore 52 and through the valve member openings 65 into the open proximal end of the cartridge cap bore 174. From bore 174, the gas flows across the exposed surface 178 of the wick 124 and through the core stem 138. From the core stem 138, the gas flows out of the cartridge, through the bore 104 of the oiler housing cap 94 into the inlet line 32.

As a consequence of the flow of gas past the wick exposed surface 178, fluid (both gaseous and liquid-state) in the wick chamber 170 and oil reservoir 122 are, by induction, drawn into the gas stream flowing to the handpiece 24. This drawing out of oil from wick 124 decreases the extent to which the wick is saturated. Since sleeve 150 is saturated with oil, replacement oil is then drawn out by capillary action from sleeve 150 and through nib 158 and the wick body 156 to the exposed wick surface 178. Thus, the gas stream delivers a generally constant aerosol of the oil to the handpiece 24 that lubricates the motor 26.

The actual rate at which oil flows from reservoir 120 into the wick chamber 135 and through wick 124 is a function of the size of hole 132 and the overall dimensions of wick 124 including nib 158. The sizing of these components may be adjusted by empirical design to achieve an optimal delivery rate.

It should be further understood that, when pressurized gas starts to flow through oiler 22 of this invention as part of the initial actuation of the handpiece 24, a small fraction of the gas flows through the wick chamber 170. This gas also flows through the annular channel 151, around sleeve 150, and into the gas reservoir 152. This gas forms a pressure charge in the reservoir 152. As long as the handpiece is actuated, the gas forming this pressure charge prevents a vacuum from forming in the oil reservoir as the lubricant is drawn out of the sleeve 150.

When the handpiece 24 is deactivated, the flow of pressurized gas through the oiler 22 and inlet line 32 to motor 32 ceases. Immediately after this flow stops, the charge of pressurized gas remains in the cartridge gas reservoir 152. To equalize pressure, the gas vents from the cartridge 40. Initially, the venting gas flows in the annular channel 151 between the porous sleeve 150 and the inner surface of the cartridge housing 116. A fraction of the venting gas then enters the distal end of sleeve 150. This gas forced a volume of oil in the distal end of the sleeve onto the wick nib 158. The remaining fraction of the venting gas flows in the narrow boundary space between the distal end of the sleeve and the rearward facing surface of the cartridge end plate 128. This gas also flows around the wick nib 158 through opening 132 into the wick chamber 135. This gas educes the oil deposited on the nib 158 onto the wick body 156.

Thus, the venting of gas from reservoir forces a volume of oil on the wick 124. Some of this oil is discharged as a bolus across wick surface 178. This oil is deposited along the inner wall of the core stem 138. The next time the handpiece motor 26 is cycled on, the oil forming this deposit is entrained in the head of the pressurized gas stream applied to the motor. The oil is then applied to the internal components of the motor 26 when the pressure head reactuates the motor. This oil lubricates the motor 26 when it is initially cycled back on.

The remaining fraction of the oil forced onto the wick as a consequence of the gas venting step remain in the wick. When the handpiece motor 26 is cycled on, this oil, since it is already in the wick 124, is available to be immediately entrained into the post-pressure head flow of gas to the motor 26.

Thus, the oiler of this invention both delivers a charge of oil to the motor being actuated with the initial pressure head of gas and ensures that oil will be entrained into the immediately following gas stream. Individually and collectively, these features of the ensure that when the motor is cycled oil is delivered to the motor to provide the required initial lubrication.

Moreover, as described above, during the discharge of the gas charge in reservoir 152 not all of the pressurized gas forming the charge is discharged through the oil reservoir 120 and sleeve 150. A fraction of this pressurized gas flows around the sleeve 150. This feature of the invention prevents the venting gas from forcing a large quantity of oil onto the wick. The attenuation of the through-the-sleeve gas discharge ensures that the oil deposited on the wick is not itself beyond what is needed to provide initial lubrication to the handpiece motor 26. The preventing of the discharge of an excessive volume of oil prevents excessive lubrication of the motor 26 and conserves the draw of oil from the cartridge 40.

Another feature of this invention is that, unless a cartridge 40 disposed in housing 38, valve assembly 62 is in the closed state. This prevents the actuation of the handpiece 22 unless a cartridge 40 is fitted to the housing 38.

Figure 10:
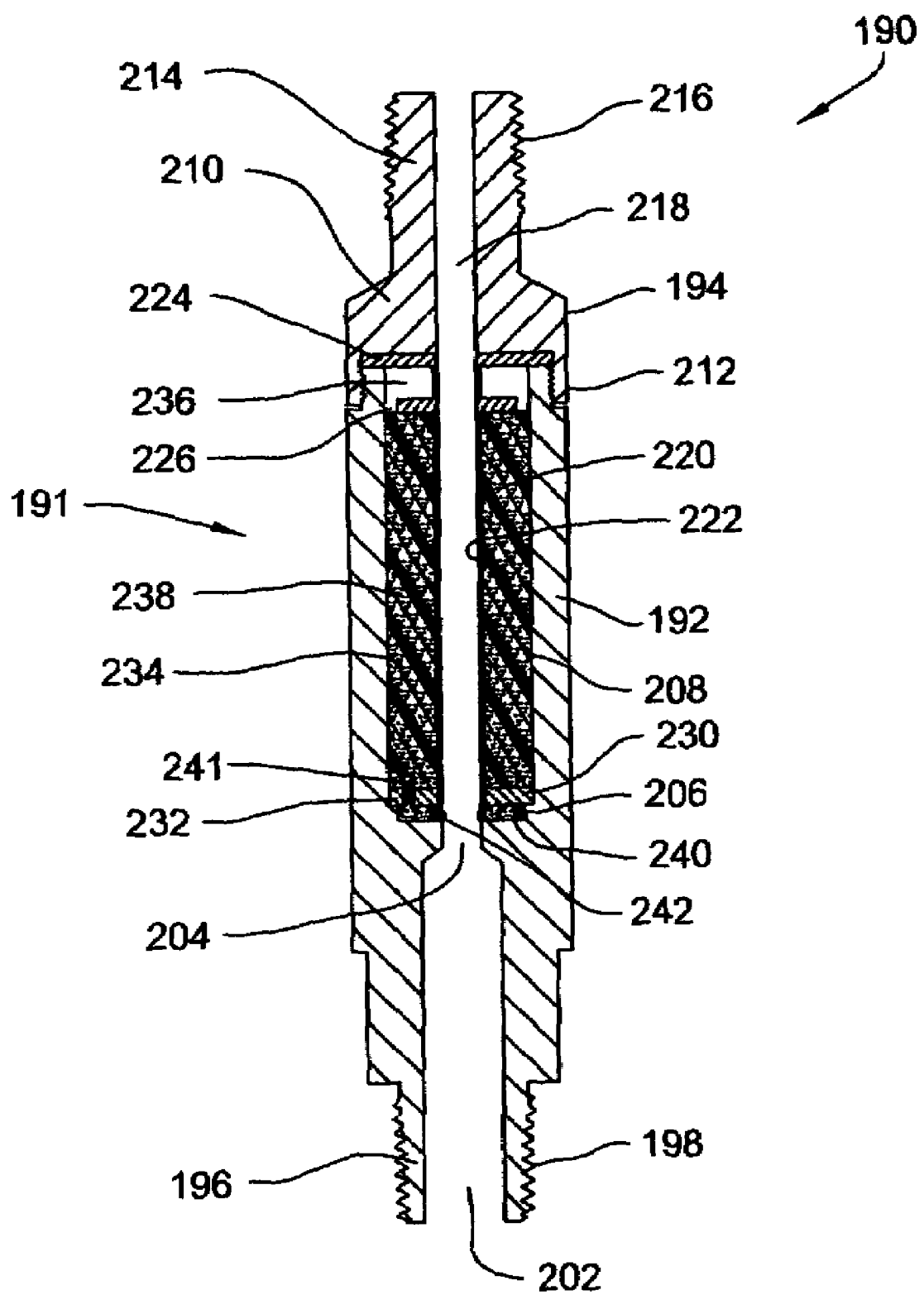
FIG. 10 is a longitudinal sectional view of an alternative oiler assembly of this invention.

FIG. 10 illustrates an alternative oiler 190 constructed in accordance with this invention. Oiler 190 includes a housing 191 that consists of an elongated, sleeve like base 192 to which a cap 194 is attached. Base 192 is formed to have a tail 196 that forms the proximal end of the oiler 190. The tail 196 is provided with exterior threading 198 for coupling the oiler to the footswitch assembly 34 or other gas source.

The base 192 is further formed to have a multi-section bore that extends axially through therethrough. Specifically the bore has a first proximal section 202 that forms the proximal end opening into the oiler 190. Extending distally from the proximal section 202, the base is formed so that the bore tapers, (taper not identified) into a neck 204. The bore neck 204 has a diameter less than that of proximal section 202. Immediately distal to neck 204, the base 192 is formed to define a wick chamber 206. Wick chamber 206 has a constant diameter that is greater than that of the bore neck 204. Integral with and extending distally from the wick chamber 206, the base has a bore distal end section 208. Bore distal end section 208 has a constant diameter that is greater than the diameter of the wick chamber 206. The distal end section 208 extends to the distal end of the base 192. In the illustrated version of the invention, bore distal end section 208 extends approximately one-half the total length of the base 192.

The oiler cap 194 has a relatively large diameter base 210. A lip 212 extends distally downward from base 212 and has an outer diameter equal to that of the base 210. The outer surface around the proximal end of oiler base 192 and the inner surface of lip 212 are formed with complementary threading, not identified, to facilitate the screw securement of the cap 194 to the base 192. In the depicted version of the invention, the distal end of the oiler base 192 has a diameter slightly less than the diameter of the immediate proximal section of the base 192. The threading is formed on this circular surface. This makes it possible to provide an oiler 190 with a cap base 210 and lip 212 that have a common outer diameter equal to the outer diameter of the immediately proximal section of the oiler base 192.

The oiler cap 194 is further formed to have a neck (not identified) with an outer diameter that tapers inwardly. The neck tapers into a constant diameter head 214 that forms the distal end of the oiler 190. The outer surface of the head is formed with threading 216. Threading 214 is for the screw securement of a connector at the proximal end of the inlet line 32 to the oiler 190.

Cap 194 is formed with an axially extending constant diameter through bore 218. When the oiler 190 is assembled, the cap bore 218 is coaxial and in fluid communication with the multi-section bore that extends through the oiler base 192.

A core 220 is disposed in the bore distal end section 208 of the oiler base 192. Core 220 has a sleeve-shaped stem 222 that extends substantially, but not completely, through the bore distal end section 208. A flat, washer shaped head 224 is formed integrally with and extents around the distal end of the stem 220. The core head 224 has an outer diameter equal to the outer diameter of the reduced diameter distal end of the oiler base 192. Core 220 has a flat, washer shaped shoulder 226 also integral with and extending laterally away from the stem 222. The core 220 is formed so that shoulder 226 is spaced longitudinally proximally away from the core head 224. Core shoulder 226 has a diameter less than that of the bore distal end section 208 of the oiler base 192.

When oiler 190 is assembled, the core 220 is positioned so that the core head 224 is disposed over the distal end of the base 192. Core head 224 is sandwiched between the distally-directed face of the oiler base 192 and the proximally-directed circular surface of the cap base 210 circumscribed by lip 212. While not illustrated, it should be appreciated that, in some versions of the invention, a washer-shaped seal is disposed against one surface of the core head 224 and the adjacent oiler component. In versions where the seal is present, it is typically located between the core head and the adjacent ring-shaped distally-directed face of the oiler base 192. Alternatively, a washer-shaped seal may be substituted for the core head 224.

A washer-shaped end plate 230 is disposed in the proximal end of the base bore distal end section 208. End plate 230 thus forms the distal end cover of the wick chamber 206. A through hole 232 extends axially through the end plate 230. Collectively, the oiler base 192, the core 220 and end plate 230 are dimensions so that the proximal end of the core stem 222 terminates at or near the through hole 232 of end plate 230. In some versions of the invention, the proximal end face of the core stem 222 abuts against the distally-directed portion of end plate 230 that defines the through hole. In alternative versions of the invention, the proximal end of the core stem is seated in and terminates in the through hole 232. In these versions of the invention, the outer surface of the core stem 22 may be formed with an outward taper to facilitate the close contact fit of the stem against the adjacent surface of the end plate 230 that defines through hole 232.

The space within the distal end section 208 of the oiler base bore between the core stem 222 and the inner wall of the bore and between the core shoulder 224 and the end plate 230 functions as the oil reservoir 234 of oiler 190. The annular space between the core head 224 and core shoulder 226 functions as a gas reservoir 236.

A foam sleeve 238 is disposed in the oil reservoir 234. Sleeve 238, like sleeve 150, is saturated with oil suitable for lubricating the handpiece motor 26. While not seen, it should be recognized that the sleeve 150 is dimensioned to form an air channel between the proximal end of the sleeve and gas reservoir 236.

A wick 240 is disposed in wick chamber 206. The main, washer-shaped body of the wick 240 is sandwiched between the interior surface of the core base 192 that defines the wick chamber 208 and end plate 230. Wick 238 is formed with a distally directed nib 241. Nib 241 extends through an axially offset opening in the end plate 230 into the oil reservoir 236 (opening not identified). The nib 241 is in contact with sleeve 238 to facilitate the transfer of oil from the sleeve to the wick 240.

When the oiler 192 is assembled, the inner surface of the wick 240 defines part of the flow path through the oiler through which gas flows to the handpiece 24.

Oiler 190 functions in the same generally manner as the first described oiler 22. The oiler 190 is series connected with the inlet line 32 employed to supply pressurized gas to the handpiece motor 26. The gas flows into oiler 192 through the oiler base bore proximal end section 202. The gas flows past an exposed face 242 of wick 238 into the core stem 222. From the core 220, the gas flows out of the oiler through cap bore 218 into the inlet line 32.

As a consequence of the gas flowing past the exposed circular face 242 of the wick 240, oil in the wick is educed into the gas flow. The oil is delivered to the internal components of the handpiece motor 26. When the head of pressurized gas is initially flowed through the oiler 190 and inlet line 32 to actuate the motor 26, a small fraction of the gas fills the gas reservoir 236. When the motor 26 is cycled off and the flow of gas from supply 30 ceases, this charge of gas is released towards the motor. This gas charge forces oil into the wick chamber 206.

A fraction of this oil forms a bolus of oil that is deposited on the inner surface of the core stem 222. This oil functions as the initial lubricant when the handpiece 24 is reactuated. The remaining volume of oil still held in the wick 240 is then available for immediate entrainment in the gas stream that cycles the motor back on.

Figure 11:
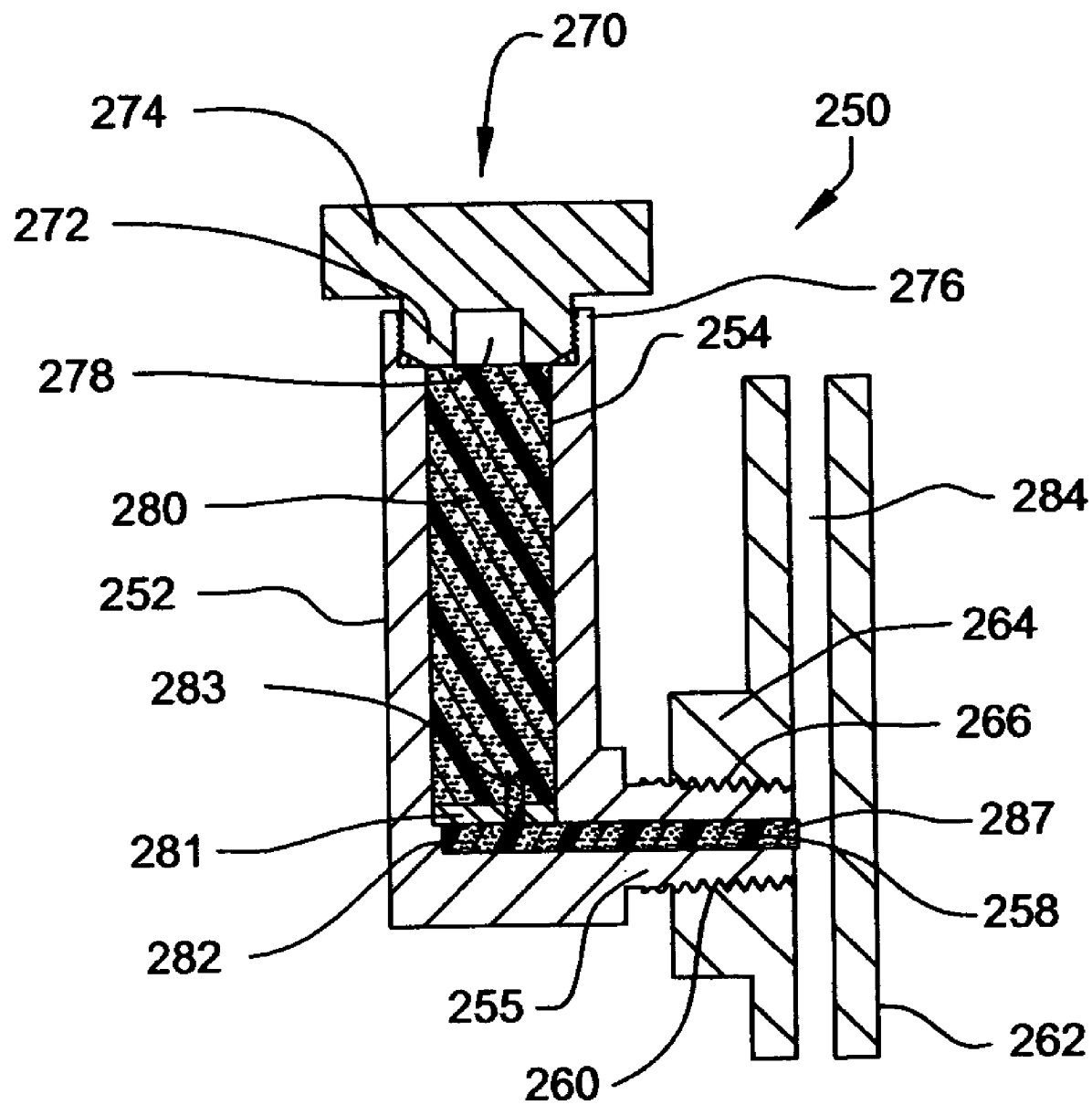
FIG. 11 is a longitudinal sectional view of a second alternative oiler assembly of this invention.

FIG. 11 depicts a third oiler 250 constructed in accordance with this invention. Oiler 250, includes a cylindrical housing 252. The housing 252 is formed to have a closed-end bore 254. Immediately above the base of the housing 252, oiler 250 has a finger 255. Finger 255 is formed integrally with the housing 252 and extends perpendicularly away from the longitudinal axis of the housing. The finger 255 is formed to have a bore 258 that extends inwardly from free end of the finger towards housing bore 254. In the depicted version of the invention, finger bore 258 terminates at a location immediately below the base of the housing bore 254 and is contiguous with the housing bore 254. Finger bore 258 functions as the wick chamber for oiler 250.

The outer surface of finger 255 is formed with threading 260. The threading 260 facilitates the screw securement of the oiler 250 to a rigid tube 262 that forms part of the flow conduit for the gas supplied to the handpiece 24. In the depicted version of the invention, tube 262 has a boss 264 that extends laterally away from the flow axis through the tube. The boss 264 is formed with a threaded bore 266 into which finger 256 is screw secured.

A cap 270 is screw secured over the open end of the housing bore 254. In the illustrated version of the invention, cap 270 has a base 272 and a head 274 that are formed integrally with each other. The base 272 has an outer diameter that is less than the outer diameter of the cap head 274. The outer cylindrical surface of the base 272 is formed with threading, not identified. The open end of the housing 252 is formed with a threaded counterbore 276 in which the cap base 272 is screw secured. Cap 270 is further formed to define base a closed-end bore 278 that is open to and contiguous with the housing bore 254.

Oiler 250 is constructed so that the housing bore 254 functions as the oil reservoir. A cylinder 280 formed of the same material used to form sleeves 150 and 238 is seated in the housing bore 254. Cylinder 280 is saturated with the lubricating oil. A circular end plate 281 is seated in the base of the housing bore 254 below the cylinder 280. End plate 281 separates the housing bore 254 from the finger bore 258. Bore 278 defined by the cap 270 functions as the gas reservoir.

A rod-shaped wick 282 is disposed in the finger bore 258. Wick 282 is dimensioned to extend from the closed-end base of the bore 258, through the bore, and to project a slight distance out of the bore 258. Thus, wick 282 has an exposed end 287 that projects into the conduit 284 defined by tube 262 through which the pressurized gas is supplied to the handpiece 24. Wick 282 also has a nib 283 at the proximal end. Nib 283 extends through an opening in the end plate 281 to contact cylinder 280 (end plate opening not identified).

When the handpiece 24 to which oiler 250 is attached is cycled on, the pressurized gas is supplied to the handpiece motor 26 through tube 262. The gas flow past the exposed head of the wick 282 educes the flow of oil out of the oil-saturated cylinder 280 and the wick. The oil is transported to the internal components of the handpiece motor 26.

When the gas is flowed to the handpiece 24 to initially actuate the motor 26, a small fraction of the gas flows into the oiler 250. A parcel of this pressurized gas occupies the gas reservoir-forming cap bore 278. When, upon cycling off of motor 26, gas flow to the handpiece 24 is terminated, the gas in the gas reservoir flows out. This vented gas forces a quantity of oil onto wick 282. A fraction of this oil is discharged onto the inner walls of tube 262. This oil becomes entrained in this pressure head of gas stream employed to cycle the motor 26 back on. The remaining oil in the wick 28 is educed out of the oiler 250 in the gas stream immediately following this pressure head.

The foregoing description is directed to specific versions of the invention. It should be appreciated that other versions of the invention may have features different what has been described.

For example, the first described version of the invention, is illustrated as having a single hole 132 that forms the fluid communication path between the oil reservoir and wick chamber 135. Alternative versions of this invention may have plural holes 132 or one hole 132 that may be larger in diameter than hole 130. In versions of the invention with plural holes 132, the associated wick 124 will have plural nibs 158. Each nib 158 extends through a single hole 132. The collective size of the opening defined by the hole/holes 132 may be determined by experimentation for the particular design of the oiler.

Also, while not illustrated, it should be understood that in many preferred versions of the invention, sleeves 238 and 280 are dimensioned to define flow through channels similar to channel 151 of the first embodiment. In versions of the invention where, the oil soaked sleeve forming the oil reservoir surrounds a core or other through conduit. The through channel may be between the sleeve and the core.

Similarly, the housing in which the oil-soaked member and gas is flowed of oiler 250 are illustrated and described as being the actual oiler housing. In alternative versions of the invention, this housing may be a replaceable cartridge. At a minimum, the cartridge will comprise the oil reservoir and gas reservoir. Alternatively, the cartridge includes the wick chamber. In these versions of the invention, the cartridge may be removeably locked to the base unit by a cap similar to the housing cap 94 of the first oiler 22. Alternatively, the cartridge and base may be formed with complementary threading to facilitate the screw securement of the cartridge to the base. Still another alternative means for releasably securing the cartridge to the base may include a ball in groove assembly similar to that employed to secure cap 94 to the rest of the oiler housing. In these versions of the invention, the cartridge is provided with circumferential groove in which the locking bearings seat.

In the above versions of the invention, it may be possible to provide a valve assembly that blocks gas flow through the tube 262 when a cartridge is not mounted to the base. Specifically there may be a sliding valve plate. The plate is normally biased to prevent gas flow through tube 262. The seating of the cartridge in the base serves to displace the plate into an open state in which gas can flow through it and the tube 262.

Materials different from what has been described may serve as the media that is saturated with oil or the wick. Examples of such materials include: porous plastic; porous metal; fiberglass; wool; felt; cotton; and fiber cellulose material. These materials may also be employed as the wick chamber wick. Furthermore, the oil-saturated member may have a design different from what has been described to provide the flow-through channels from the proximal end of the member to the gas reservoir. For example, in some versions of the invention, the oil-saturated member may be formed with one or more through bores. These through bores function as the substantially oil-free conduits to the gas reservoir. This design is expected to be employed most often in versions of the invention wherein the oil saturated member is formed from solid or relatively incompressible material. Some of these components may even have closed end bores. Such design may be necessary if it is desirable to flow a quantity of gas to the distal end of the member in order to ensure the forcing of an appropriate volume of oil into the downstream wick chamber.

Moreover, there is no requirement that all versions of the invention be supplied with a wick. In some versions of the invention, the oil soaked material may be positioned so that a face of the material is located in-line with the conduit through which the pressurized gas stream is delivered to the handpiece motor 26. Alternatively, the oiler may be constructed with a housing in which the oil reservoir is located and a conduit that extends from the reservoir. This conduit functions as the wick chamber. The conduit opens into the conduit through which the gas is flowed to the handpiece 24. In some versions of the invention, the conduit is not provided with a wick. Instead, the induction flow of gas out of the conduit and the oil reservoir draws the oil out of the reservoir.

Nevertheless, it is believed most preferred versions of the invention will have a wick. This is because the wick dampens the flow of oil that is discharged from the oiler. This dampening of oil flow may be critical if a large pool of oil collects at the base of the oil-saturated member. In some versions of the invention, it is believed gravity causes such an oil pool to form.

It is also possible to provide a version of this invention wherein the oil reservoir is not provided with a oil-saturated member. In these versions of the invention, gas flow into and out of the gas reservoir may be controlled by pressure-actuated valve members. A first pressure set valve member would allow gas to flow into the gas reservoir. This valve opens when the high pressure gas stream is initially applied to the handpiece motor 26. A second pressure-set valve is connected between the oil and gas reservoirs. This valve opens after the high pressure gas flow is turned off. The second valve allows the charge of pressurized gas to flow into the oil chamber upon the deactivation of the motor 26 so the charge can deliver the bolus of oil to the motor.

Similarly, there is no requirement that, in all versions of the invention, the rigid structural components of the oiler of this invention be formed from metal. Components such as cartridge housing 118, housing base 192 and housing cap 192 may be formed from plastic. These components, for example, may be formed from injection-molded plastic.

It is contemplated that, in the above version of the invention, the oil or other lubricant is introduced into the gas stream through a wick. The wick regulates, dampens, the flow of oil. In some variations of the invention, a porous member similar to cylinder 280 is between the reservoir holding the liquid-state oil and the wick. This porous member, which is saturated with the oil, regulates the rate at which the oil flows to the wick. By limiting the extent to which the wick is saturated, this porous member attenuates the volume of oil that is educed into the gas flow.

Also, other constructions of the invention may have more or less physically separate chambers than what has been described. In some versions of the invention, the oil reservoir and gas reservoir may comprise the same contiguous void space. This space, for example may be a single, undivided annular or cylindrical space. In these versions of the invention, the oil-saturated member occupies less than the whole of the space. The space occupied by this member functions as the oil reservoir. The adjacent unoccupied space functions as the gas reservoir. Thus, in the first embodiment of the invention, instead of having a distal located gas chamber relative to the air chamber, the gas chamber comprises a void space that is laterally adjacent the oil chamber, the space occupied by sleeve 150. The gas chamber fully or partially surrounds the oil chamber. In this version of the invention it should be appreciated that the oil saturated member defining the oil reservoir is positioned to at least partially cover the opening to the inlet line 32

In still other versions of the invention, there may be multiple oil reservoirs. Structural members separate the individual reservoirs. Plates similar to end plate 230 separate the individual chambers. Each of these individual chambers may have its own lubricant soaked member. An advantage of these versions of the invention is that the individual oil chambers can be provided with different types of oil-saturated members. For example, the oil reservoir most distal from the exposed surface through which the oil is discharged may be of the type that can hold a large capacity of oil. The more proximal reservoir would have member formed from relatively dense material. The presence of this proximal member dampens the flow of oil out of the cartridge to prevent the rapid discharge of the oil.

In some versions of the invention, it may even be possible to provide an oiler wherein there is no oil saturated sleeve in one of the plural oil reservoirs. Most likely, this would be the reservoir most distal to the exposed surface through which the oil educed out of the oiler. The more proximal reservoir/reservoirs is/are provided with the porous member/members that regulate oil discharge. An advantage of this version of the invention is that a large volume of oil is held in the member-free reservoir.

Also, in some versions of the invention, the oil reservoir and the wick chamber may be a single void space. In these versions of the invention, the wick, formed of a first porous material is disposed at the base of the chamber and has a section that extends through an outlet opening to form an exposed face. The oil-saturated member abuts the wick. The oil-saturated member is formed from a second material more porous than the material forming the wick.

Also, in versions of the invention, wherein an interior wall separates the wick chamber from the oil reservoir, it may not be necessary to provide a porous member such as wick nib 158 to facilitate or regulate flow between the chambers. It is, however, anticipated that in most versions of the invention, such a structure will be required. One such a component is provided, there is no requirement that it always be integral with the wick. In some versions of the invention, this nib may form part of the oil soaked member that serves as the oil reservoir. In still other versions of the invention, this nib may be a component of porous material that is separate from both the wick and the oil soaked member.

Moreover, while threaded members are shown as coupling the oiler to a gas source 30, footswitch assembly 34 and inlet line 32, other means may be employed. For example, ball-in-groove assemblies may be employed to facilitate these connections. In these versions of the invention, the oiler components may be provided with either the ball members that are extended and retracted to perform the lock and release function of the grooves in which the balls seat.

There is no requirement that in all versions of the invention wherein the pressurized gas flows through the cartridge, that a cap be employed to hold the cartridge in place. In some versions of the invention, the distal end of the gas line may directly connect to the cartridge. In these versions of the invention, one of the above-described locking mechanisms may be employed to releasably hold the cartridge to the base unit, that is, the unit to which the gas from supply 30 is applied.

It may be desirable in some versions of the invention to directly build the oiler assembly of this invention into either the gas supply 30 or the footswitch assembly 34. Thus, one of these units could contain a housing for releaseably holding the oil cartridge 40.

Similarly, there is no requirement that in all versions of the invention wherein the gas flow is through a pipe member integral with the housing, the in-line flow assemblies, that the conduit-defining pipe member be centered along the longitudinal axis through the housing. There may be assembly reasons why this conduit is located to one side of the longitudinal axis of the housing.

Similarly, there is no requirement that in all versions of the invention, the three separate chambers be longitudinally aligned. In some versions of the invention, the chambers may be arranged side-by-side. The fluid connections are along one or more lateral axes. Thus, the oil reservoir may surround the wick chamber and/or the gas reservoir may surround the oil reservoir.

Also, while the invention is primarily described for use with surgical handpieces, it should be understood that this is illustrative and not limiting. The invention may be employed as a lubricating system for other pneumatic motors and drive assemblies. For example, this invention may be used to provide lubricant to the one or more pneumatic motors that are integral with CNC machine tools and hand-held, pneumatic motor driven machine tools such as grinders and drills.

Therefore, it is an object of the appended claims to cover all such variations and modifications that come within the true spirit and scope of this invention.

What is claimed is:

1. An oil cartridge for use with a surgical tool oiler assembly, said oil cartridge including:

a housing having a void space and opposed first and second ends, said housing dimensioned to seat in an oiler assembly that supplies gas to a pneumatically driven surgical handpiece;

first and second caps, said first cap being disposed over the first end of said housing and having a feature for opening a valve integral with the oiler assembly, said second cap being disposed over the second end of said housing, said caps having coaxial openings through which gas is flowed to the surgical handpiece;

a stem that extends from the opening in the second cap, through the housing void space towards the first cap and that terminates in said housing at a position spaced from said first cap so as define in said housing a gap between said first cap and said stem, said stem having a through bore;

a plate disposed in the housing void space that is spaced from said first cap so as to divide the void space into a wick chamber located adjacent said first cap and a oil reservoir spaced from said first cap, said plate having a first opening in which said stem is at least partially seated and a second opening that extends between the wick chamber and the oil reservoir;

a porous member disposed in said oil reservoir, said porous member holding lubricant for lubricating the surgical handpiece;

a structural member disposed in said housing for holding said porous member away from said second cap so as to define in said housing a gas reservoir between said second cap and said porous member, said gas reservoir being in fluid communication with the oil reservoir; and a wick formed from porous material disposed in the wick chamber, said wick having an exposed surface adjacent the gap between said first cap and said stem.

2. The oil cartridge of claim 1, wherein said stem extends through said plate and has an end disposed in the wick chamber.

3. The oil cartridge of claim 1, wherein
one of said wick or said porous member includes a nib that extends through the plate second opening to the other of said porous member or said wick.

4. The oil cartridge of claim 1, wherein said wick includes an opening that extends between the first cap opening and the bore of said stem and a portion of said wick that defines the wick opening defines the exposed surface of said wick adjacent the gap between said first cap and said stem.

5. The oil cartridge of claim 1, wherein:
said housing has an inner surface that defines the portion of the void space forming the oil reservoir; and
said porous member is a porous sleeve that is disposed over said stem and extends towards the housing inner surface and that is spaced from the housing inner surface so as to define a channel between said housing and said sleeve that extends to said gas reservoir.

6. The oil cartridge of claim 1, wherein said stem is formed as a single piece component.

7. The oil cartridge of claim 1, wherein:
said housing and said plate are formed as a single component; and
said first cap is formed separately from said housing and said plate and is disposed over said plate.

8. The oil cartridge of claim 1, wherein said sleeve is shaped to be spaced inwardly from an inner wall of said housing so as to define a channel between said housing and said sleeve that opens into the gas reservoir.

9. An oil cartridge for use with a surgical tool oiler assembly, said oil cartridge including:

a housing having a void space and opposed first and second ends, said housing dimensioned to seat in an oiler assembly that supplies gas to a pneumatically driven surgical handpiece;

first and second caps, said first cap being disposed over the first end of said housing, said second cap being disposed over the second end of said housing, said caps having coaxial openings through which gas is flowed to the surgical handpiece;

a plate disposed in said housing, said plate separating the housing void space into a wick chamber adjacent said first cap and an oil reservoir that is spaced from said first cap, said plate having a first and second openings, the first opening being coaxial with the openings of said first and second caps;

a stem that extends from the opening in the second cap, through the oil reservoir and at least partially through the first opening of said plate, said stem terminating in the housing at a position spaced from said first cap to define in said housing a gap between said first cap and said stem, said stem having a through bore that has an open end adjacent said first cap;

a sleeve formed of porous material disposed in the housing oil reservoir around said stem, said sleeve shaped to define a channel that extends towards said second cap and said sleeve containing lubricant for the surgical handpiece;

a structural member disposed in said housing for holding said sleeve away from said second cap so as to define in said housing a gas reservoir between said second cap and said sleeve wherein the channel defined by said sleeve extends to the gas reservoir; and a wick formed of porous material, said wick having: a main body disposed in the wick chamber that is shaped to have an opening through which gas can flow from the opening of said first cap into the open end of the stem bore, the wick opening at least partially defined by a surface of said wick adjacent the gap between said first cap and said stem; and a nib that extends from the main body through the plate second opening into the oil reservoir through which oil can flow from said sleeve to the wick main body.

10. The oil cartridge of claim 9, wherein the material forming said sleeve is more porous than the material forming said wick.

11. The oil cartridge of claim 9, wherein said structural member that defines the gas reservoir is a shoulder that projects outwardly from said stem.

12. The oil cartridge of claim 9, wherein said first cap is formed with a boss disposed around and forward of the opening of the opening in said first cap, said boss having a through bore.

13. The oil cartridge of claim 9, wherein said sleeve is spaced inwardly from said housing so that the channel is located between said housing and said sleeve.

14. The oil cartridge of claim 9, wherein:
said housing and said plate are formed as a single component; and
said first cap is formed separately from said housing and said plate and is disposed over said plate.

15. An oil cartridge for use with a surgical tool oiler assembly, said oil cartridge including:

a housing having a void space and opposed first and second ends, said housing dimensioned to seat in an oiler assembly that supplies gas to a pneumatically driven surgical handpiece;

a first cap disposed over the first end of said housing and a second cap disposed over the second end of said housing, said caps having coaxial openings through which gas is flowed to the surgical handpiece;

a stem that extends from the opening in the second cap, through the housing void space towards the first cap and that terminates in said housing at a position spaced from said first cap so as define in said housing a gap between said first cap and said stem, said stem having a through bore with an open end adjacent the first cap;

a plate disposed in the housing void space that is spaced away from said first cap to divide the housing void space into a wick chamber located adjacent said first cap and a oil reservoir spaced from said first cap, said plate having a first opening in which said stem is at least partially seated and a second opening that extends between the wick chamber and the oil reservoir;

a sleeve formed of a porous material disposed in the oil reservoir for holding lubricant for lubricating the surgical handpiece, said sleeve shaped to be spaced inwardly from said housing so as to define a channel between said housing and said sleeve that extends towards the second cap;

a structural member disposed in said housing void space to hold said sleeve away from said second cap so as to define a gas reservoir in said housing between said second cap and said sleeve wherein the channel defined by said housing and said sleeve opens into the gas reservoir;

a wick formed from porous material disposed in the wick chamber, said wick having an opening through which gas can flow from the opening of said first cap into the stem bore open end, the wick opening defined by a surface of said wick adjacent the gap between said first cap and said stem; and a nib formed from porous material that extends from the oil reservoir, through the plate second opening to said wick.

16. The oil cartridge of claim 15, wherein said nib is integrally formed with said wick.

17. The oil cartridge of claim 15, wherein said stem is formed as a single-piece component.

18. The oil cartridge of claim 15, wherein said second cap and at least a portion of said stem are formed as a single component.

19. The oil cartridge of claim 15, wherein:

said housing and said plate are formed as a single component; and said first cap is disposed over an outer surface of said plate.

20. The oil cartridge of claim 15, wherein said first cap is formed with a boss disposed around and forward of the opening in said first cap, said boss having a through bore and functioning as a feature for opening a valve integral with the oiler assembly.

* * * * *